(12) United States Patent
Li et al.

(10) Patent No.: US 9,999,249 B2
(45) Date of Patent: Jun. 19, 2018

(54) AEROSOL INHALING DEVICE

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Xingbing Zou, Shenzhen (CN); Laizhi Song, Shenzhen (CN)

(73) Assignee: SHENZHEN FIRST UNION TECHNOLOGY CO., LTD., Shezhen, Guangdong Province (CN)

( * ) Notice: Subject to any disclaimer, the term of this patent is extended or adjusted under 35 U.S.C. 154(b) by 361 days.

(21) Appl. No.: 14/698,836

(22) Filed: Apr. 28, 2015

(65) Prior Publication Data
US 2015/0305407 A1     Oct. 29, 2015

(30) Foreign Application Priority Data

Apr. 28, 2014   (CN) .................... 2014 2 0209124 U
Apr. 28, 2014   (CN) .................... 2014 2 0210693 U

(51) Int. Cl.
   *A24F 47/00*   (2006.01)
   *A61M 11/08*   (2006.01)
(52) U.S. Cl.
   CPC ........... *A24F 47/008* (2013.01); *A61M 11/08* (2013.01)

(58) Field of Classification Search
   CPC ....... A24F 47/008; A61M 11/08; A61M 15/00
   USPC ......................................... 131/273, 328, 329
   See application file for complete search history.

(56) References Cited

U.S. PATENT DOCUMENTS

| | | | |
|---|---|---|---|
| 2011/0041858 A1* | 2/2011 | Montaser | A61M 15/0085 131/273 |
| 2012/0199663 A1* | 8/2012 | Qiu | A61M 11/041 239/8 |
| 2013/0167854 A1* | 7/2013 | Shin | A24F 47/008 131/329 |
| 2013/0220315 A1* | 8/2013 | Conley | A61M 11/042 128/202.21 |
| 2013/0255675 A1* | 10/2013 | Liu | A61M 11/041 128/202.21 |

* cited by examiner

Primary Examiner — Joseph S Del Sole
Assistant Examiner — Mohamed K Ahmed Ali
(74) Attorney, Agent, or Firm — Cheng-Ju Chiang

(57) ABSTRACT

An exemplary aerosol inhaling device includes a liquid supply, an atomizing device, and a power supply. The liquid supply is configured for storing tobacco liquid. The atomizing device configured for heating the tobacco liquid to form aerosol. The power supply is electrically connected with the atomizing device. The power supply is configured for supplying the atomizing device power.

14 Claims, 9 Drawing Sheets

AEROSOL INHALING DEVICE

TECHNICAL FIELD

The present invention relates to aerosol inhaling devices.

BACKGROUND ART

Although smoking may cause serious respiratory diseases and cancer, it remains extremely difficult for smokers to quit smoking completely.

The active ingredient in a cigarette is nicotine. During smoking, nicotine, along with tar aerosol droplets, enter the smoker's alveolus and are widely absorbed. The nicotine then affects the receptors of the smoker's central nervous system.

Nicotine is a kind of alkaloid with low molecular weight. A small dose of nicotine is essentially harmless to human body and its half-life in blood quite short. The major harmful substance in tobacco is tar. Tar in tobacco is composed of thousands of ingredients. Several of these are cancerogenic.

What is needed, therefore, is a cigarette substitute, which can overcome the above shortcomings.

SUMMARY

An exemplary aerosol inhaling device includes a liquid supply, an atomizing device, and a power supply. The liquid supply is configured for storing tobacco liquid. The atomizing device configured for heating the tobacco liquid to form aerosol. The power supply is electrically connected with the atomizing device. The power supply is configured for supplying the atomizing device power.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
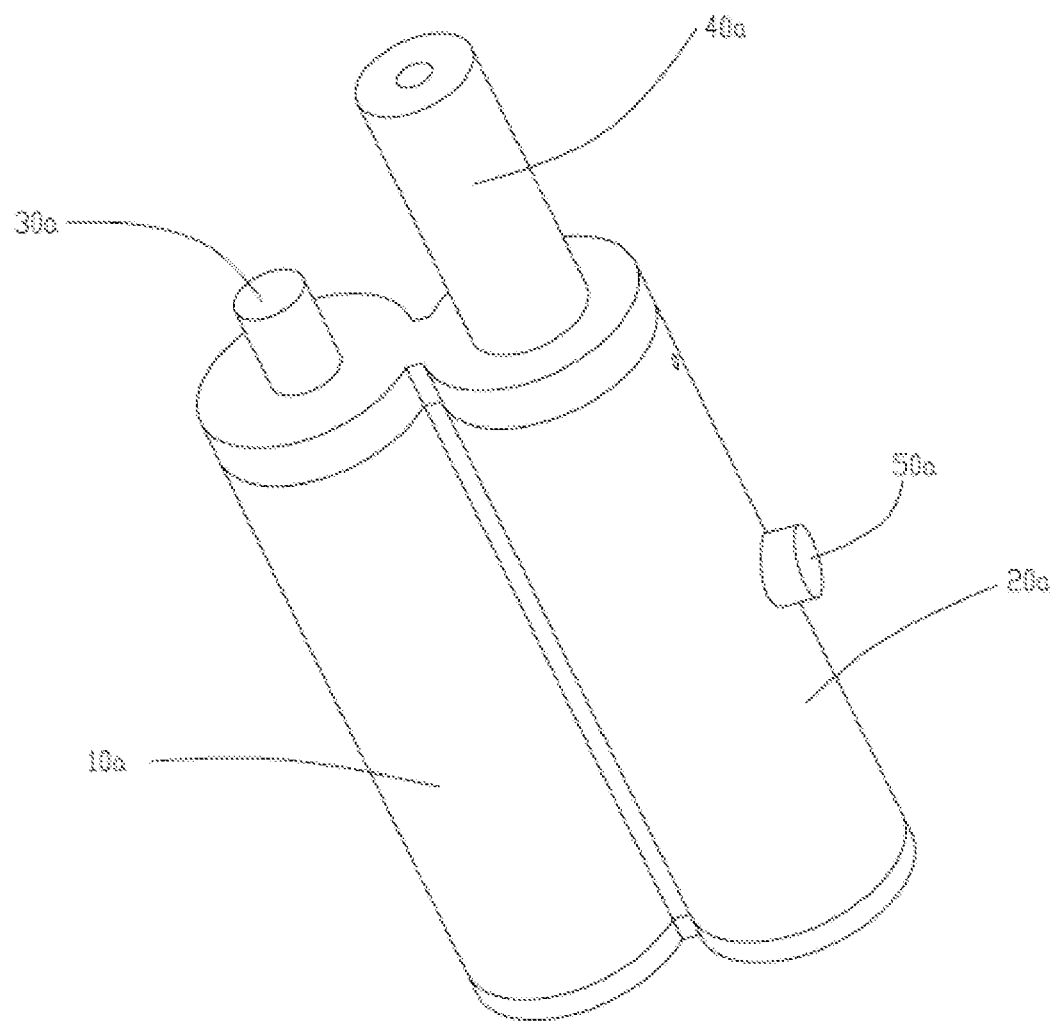
FIG. 1 is a perspective view of an aerosol inhaling device according to a first embodiment, the aerosol inhaling device including an atomizing device.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 2:
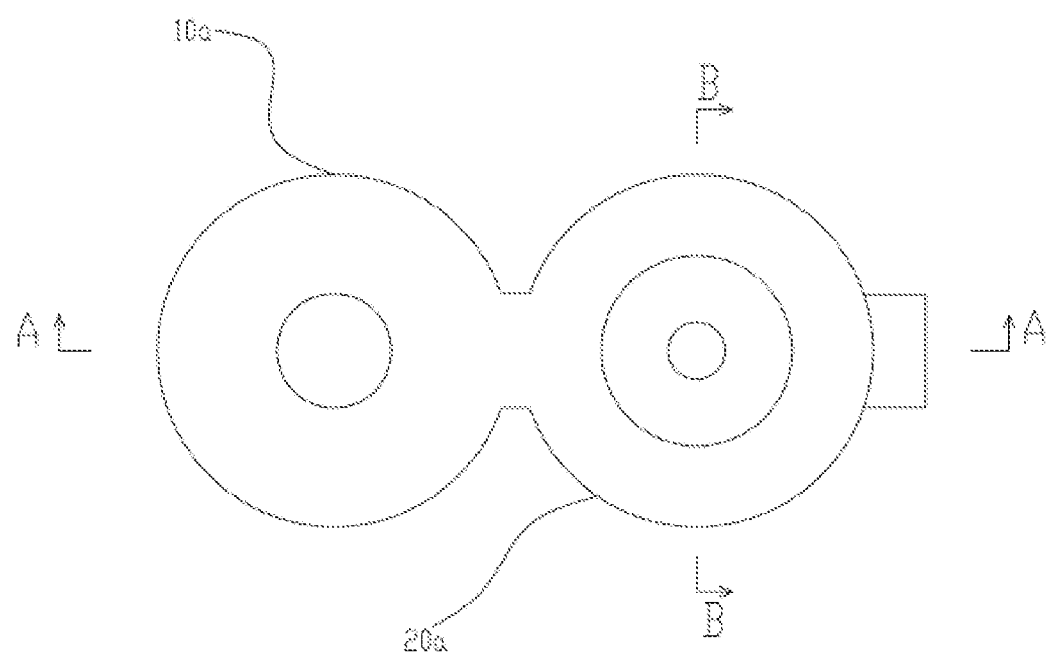
FIG. 2 is a top view of the aerosol inhaling device of FIG. 1.

Referring to FIGS. 1-2, an aerosol inhaling device includes a main body 20a and a liquid supply 10a arranged side by side along a horizontal direction.

Figure 3:
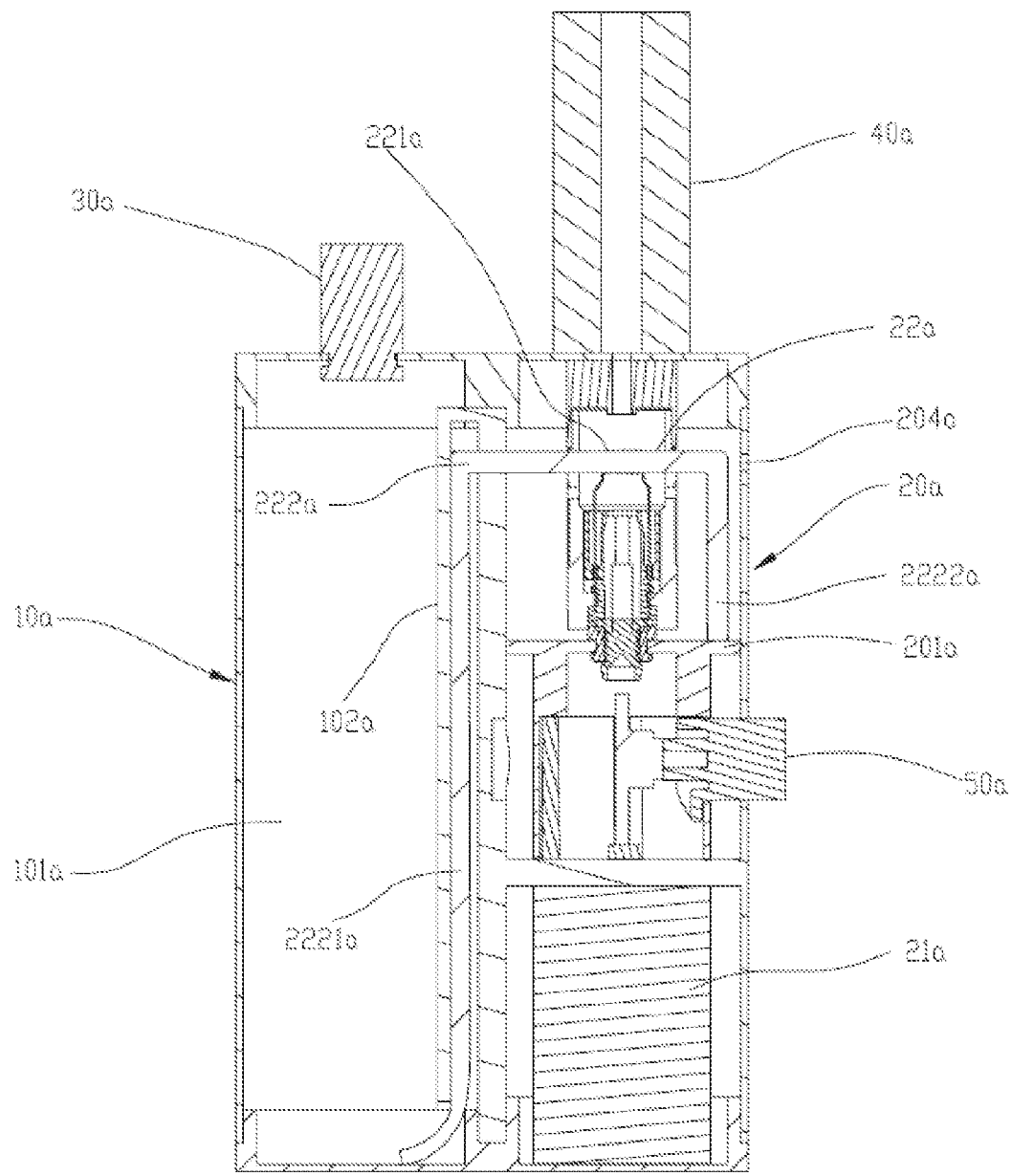
FIG. 3 is a cross-sectional view of the aerosol inhaling device of FIG. 2 taken along line A-A.
Figure 4:
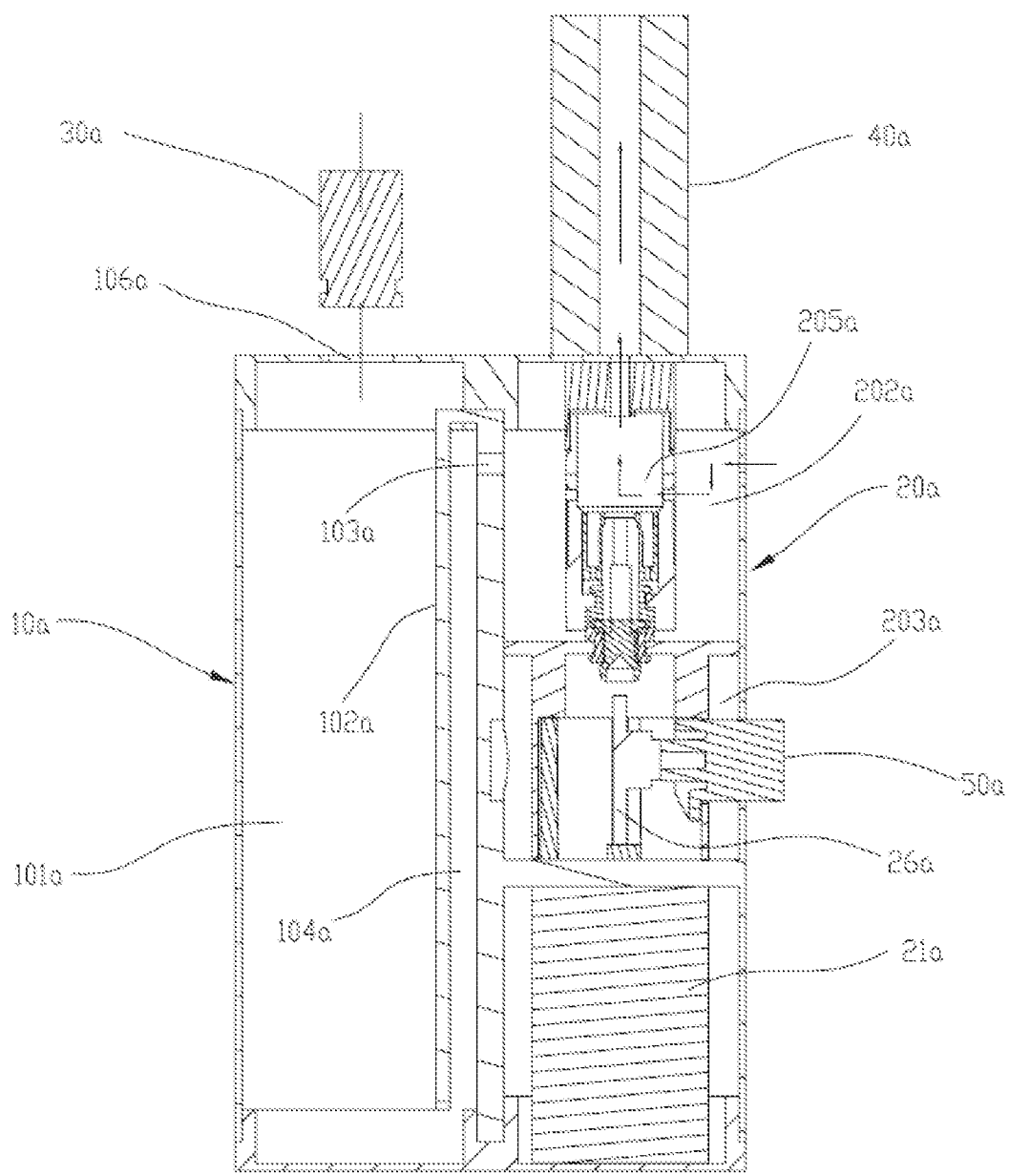
FIG. 4 is a cross-sectional view of the aerosol inhaling device, removing the atomizing device.
Figure 5:
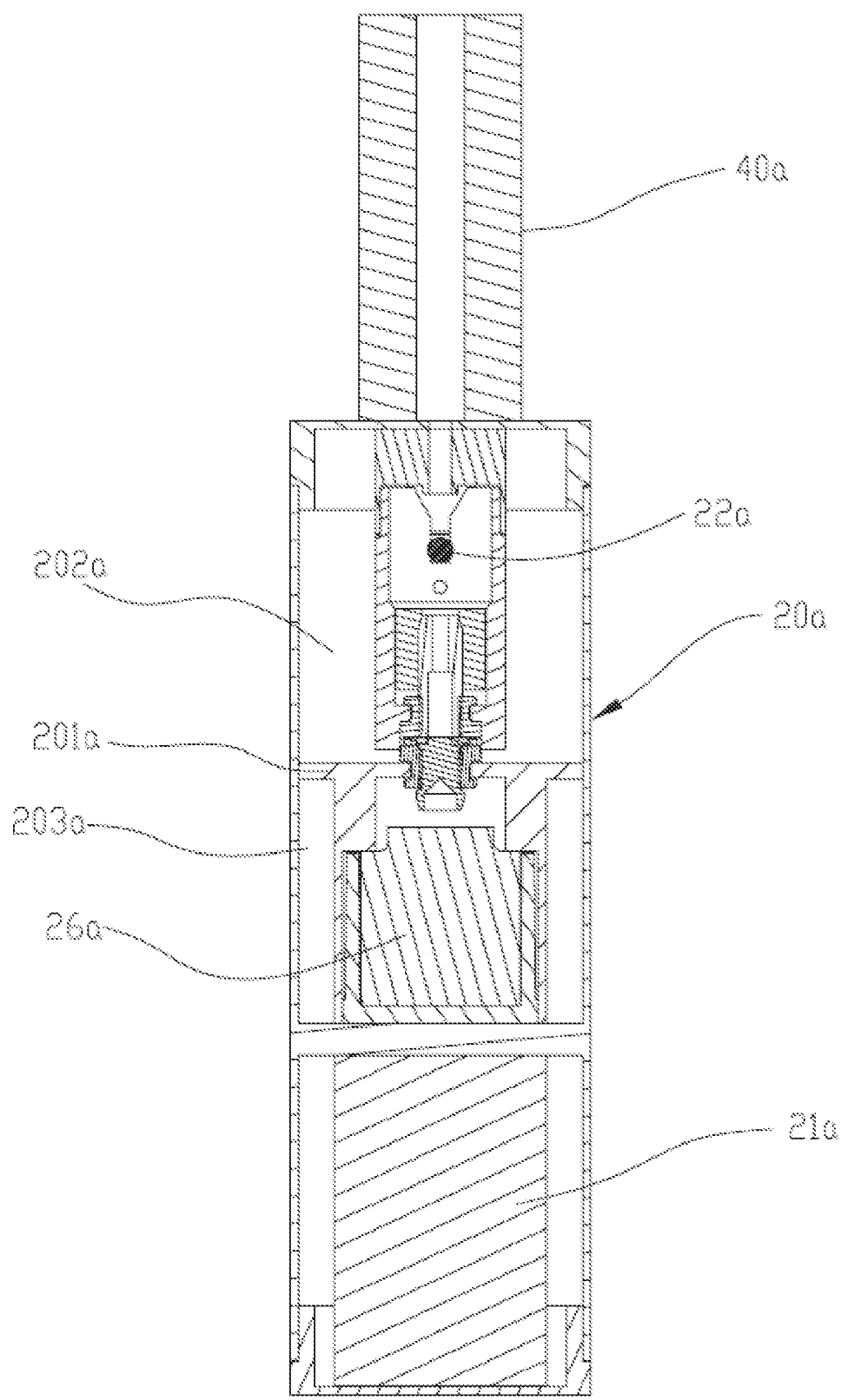
FIG. 5 is a cross-sectional view of the aerosol inhaling device of FIG. 2 taken along line B-B.

Referring to FIGS. 3-5, the liquid supply 10a includes a liquid storage space 101a and a liquid conducting space 104a. The main body 20a includes an atomizing device 22a, an air passage 205a, and a power supply 21a for supplying the atomizing device 22a power. The atomizing device 22a includes a heating element 221a, and a liquid conducting element 222a. The heating element 221a is wound around the liquid conducting element 222a, and positioned in the air passage 205a. A through hole 103a is provided, extending from the main body 20a to the liquid supply 10a. The liquid conducting element 222a extends through the through hole 103a to the liquid storage space 101a. The liquid conducting element 222a is configured (i.e., structured and arranged) for conveying tobacco liquid in the liquid storage space 101a to the heating element 221a, so that the heating element 221a heats the tobacco liquid to form aerosol. The aerosol is free of tar. In the present embodiment, the liquid conducting element 222a is made of glass fiber material. In other embodiments, the liquid conducting element 222a may be made of ceramic material.

Referring to FIG. 3, a holder 201a is provided in the main body 20a, and separates the main body 20a into a buffer room 202a and a power room 203a. The atomizing device 22a and the air passage 205a are arranged in the buffer room 202a. The power supply 21a is received in the power room 203a. The atomizing device 22a is above the power supply 21a. The buffer room 202a defines an air inlet 204a in a side wall. The air inlet 204a is arranged at a top part of the buffer room 202*a*, so that the buffer room 202*a* stores tobacco liquid dropped from the liquid conducting element 222*a*.

The liquid supply 10*a* defines a liquid filler hole 106*a* in a top part. A stopper 30*a* is provided in the liquid filling hole 106*a*. A mouthpiece 40*a* is arranged at top of the main body 20*a*, and communicates with the buffer room 202*a*. In the present embodiment, the mouthpiece 40*a* and the stopper 30*a* are made of silica gel.

A baffle 102*a* is provided in the liquid storage space 101*a*, and divides the liquid supply 10*a* into the liquid storage space 101*a* and the liquid conducting space 104*a*. The through hole 103*a* and part of the liquid conducting element 222*a* are positioned in the liquid conducting space 104*a*. In the present embodiment, the liquid storage space 101*a* communicates with the liquid conducting space 104*a*. Accordingly, when the aerosol inhaling device is inverted, the baffle 102*a* prevents a large amount of the tobacco liquid in the liquid storage space 101*a* from flowing into the buffer room 202*a* via the through hole 103*a*.

The liquid conducting element 222*a* includes a first end 2221*a* and an opposite second end 2222*a*. The first end 2221*a* extends to a bottom part of the liquid storage space 101*a*, so that the tobacco liquid in the liquid storage space 101*a* is conveyed to the heating element 221*a* for atomization. The second end 2222*a* extends to a bottom part of the buffer room 202*a*, so that tobacco liquid in the buffer room 202*a* is also conveyed to the heating element 221*a* for atomization.

Further, a circuit board 26*a* and a switch button 50*a* are arranged in the main body 20*a*. The switch button 50*a* is electrically connected with the circuit board 26*a*, and configured for turning on/off the aerosol inhaling device. The switch button 50*a* protrudes from the main body 20*a*. The circuit board 26*a* is received in the power room 203*a*.

In the present embodiment, a direction of air flow during smoking is shown as arrowheads in FIG. 4.

In use, when the switch button 50*a* is pressed down, the heating element 221*a* is powered on to heat tobacco liquid to form aerosol. A user of the aerosol inhaling device sucks the aerosol through the mouthpiece 40*a*. After the tobacco liquid in the liquid storage space 101*a* is used up, the stopper 30*a* is pulled out, and new tobacco liquid is filled into the liquid storage space 101*a* via the liquid filling hole 106*a*.

In the present embodiment, the main body and the liquid supply are arranged side-by-side along a horizontal direction. The liquid conducting element extends from the main body to the liquid supply. Accordingly, the atomizing device is separated from the liquid supply. Therefore, an amount of tobacco liquid stored in the liquid supply is increased.

Figure 6:
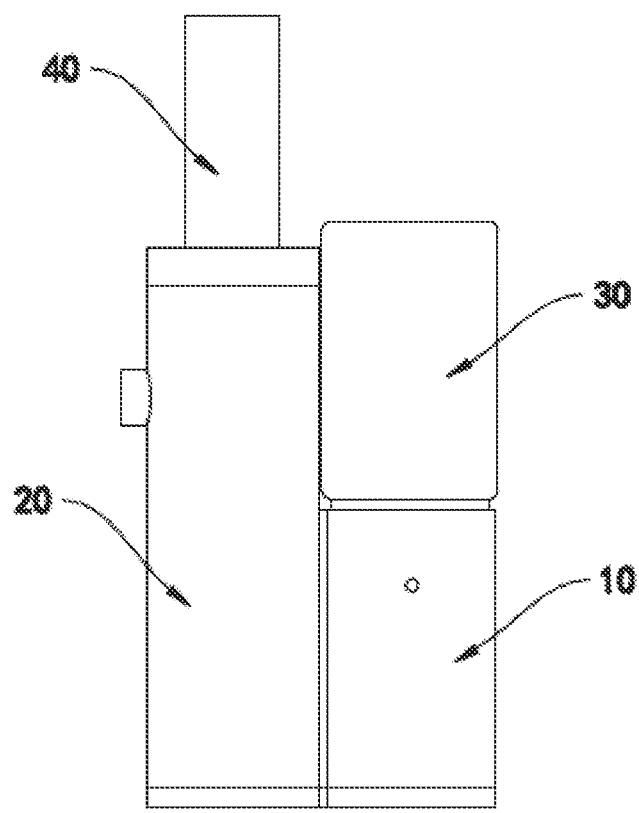
FIG. 6 is an aerosol inhaling device according to a second embodiment.

Referring to FIG. 6, an aerosol inhaling device includes an atomizing device 10, a power supply 20, a liquid supply 30 and a mouthpiece 40. The power supply 20 is electrically connected with the atomizing device 10. The liquid supply 30 is configured for storing tobacco liquid, and is detachably connected to the atomizing device 10. The mouthpiece 40 is fixedly connected to the power supply 20.

Figure 7:
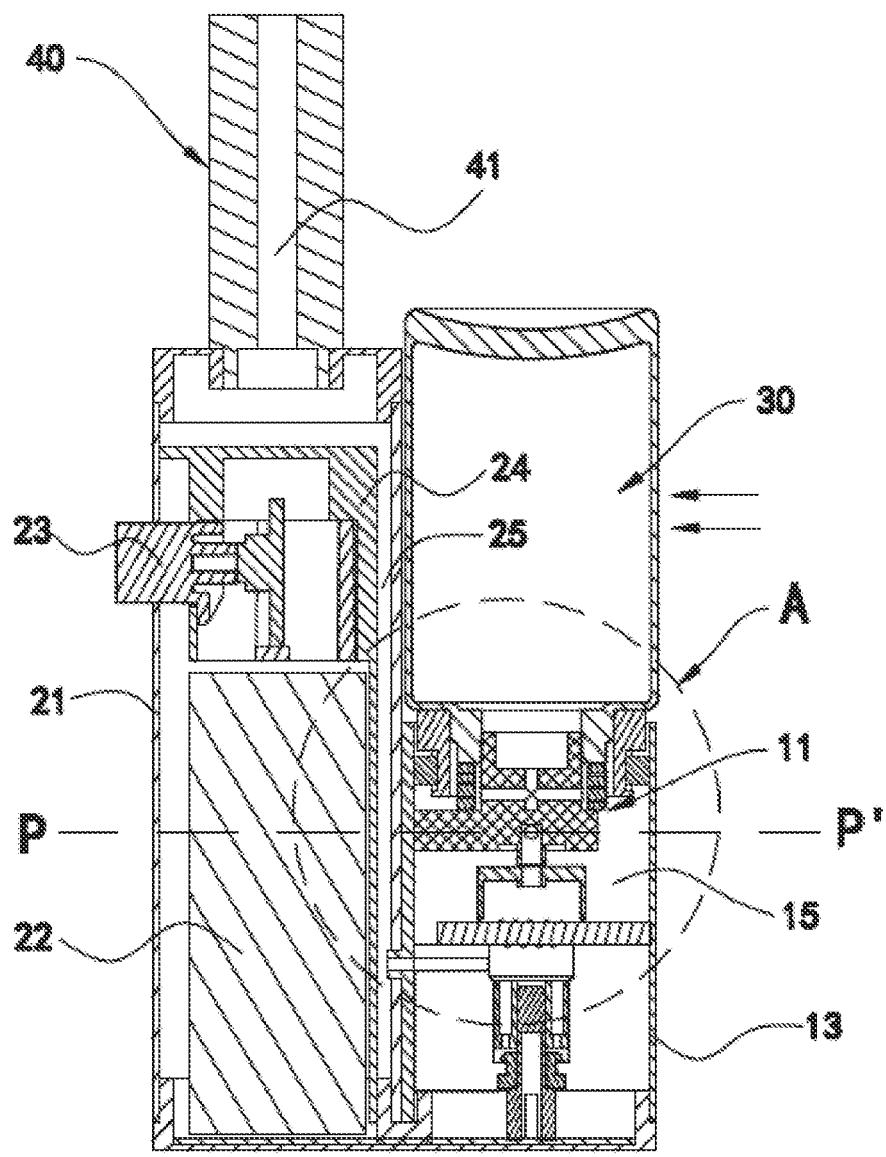
FIG. 7 is a cross-sectional view of the aerosol inhaling device of FIG. 6.
Figure 8:
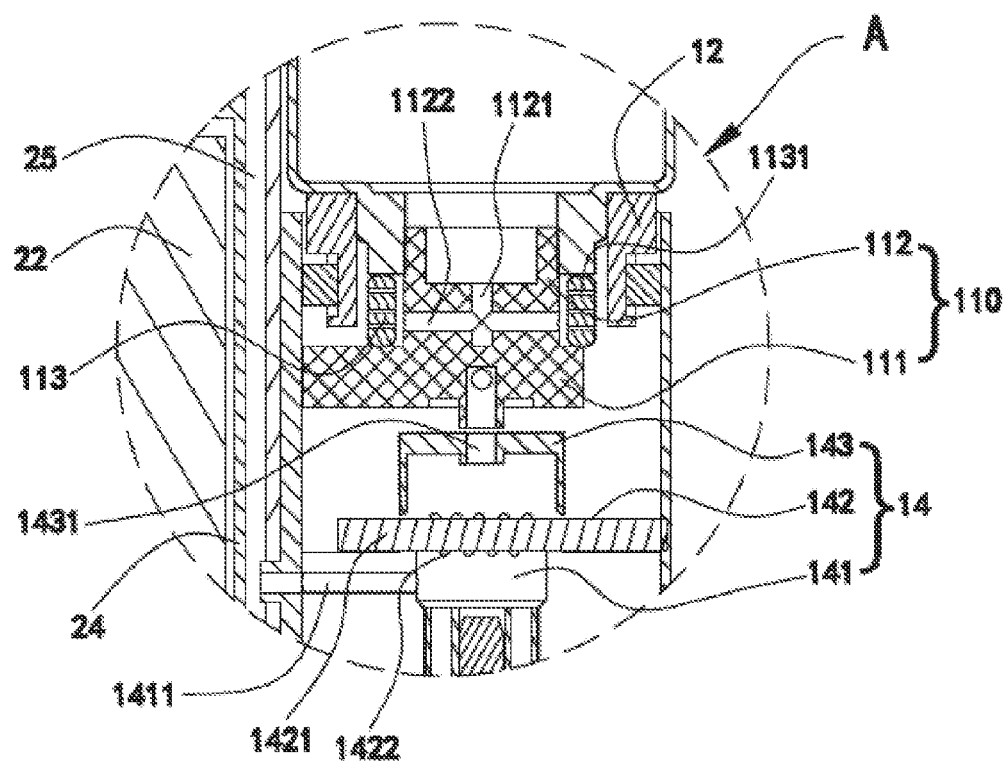
FIG. 8 is an enlarged view of area A of FIG. 7.

Referring to FIGS. 7-8, the atomizing device 10 includes a connector 12 detachably connected to the liquid supply 30. The connector 12 is capable of moving up and down relative to the atomizing device 10, so that tobacco liquid flows to the atomizing device 10 when the liquid supply 30 is pressed. In the present embodiment, the connector 12 includes a plurality of internal screw threads, the liquid supply 30 includes a plurality of external screw threads, and the connector 12 and the liquid supply 30 are coupled by screw threads.

The atomizing device 10 includes a liquid controlling assembly 11 configured (i.e., structured and arranged) for controlling tobacco liquid in the liquid supply 30 to flow to the atomizing device 10. The liquid controlling assembly 11 includes a liquid guiding element 110 fixed in the atomizing device 10, and an elastic element 113 engaged with the liquid guiding element 110. The liquid guiding element 110 includes a fixing holder 111, and a liquid guiding holder 112 extending upwards from the fixing holder 111. The elastic element 113 is engaged outside the liquid guiding holder 112, and abuts against the liquid supply 30. The liquid guiding holder 112 inserts into the liquid supply 30. The liquid guiding holder 112 defines a liquid guiding hole 1121 and a liquid guiding passage 1122 communicating with the liquid guiding hole 1121. The elastic element 113 defines gaps 1131 communicating with the liquid guiding passage 1122. The tobacco liquid flows to a liquid storage chamber 15 via the gaps 1131. In the present embodiment, the elastic element 113 is made of silica gel with gaps, and the liquid supply 30 is a resilient plastic bottle. When the liquid supply 30 is pressed, the tobacco liquid flows out from the liquid supply 30 to the liquid storage chamber 15 through the liquid guiding passage 1122, the gaps 1131. When the liquid supply 30 is not pressed, the liquid supply 30 restores to its original state, the tobacco liquid in the liquid supply 30 stops flowing due to atmosphere pressure and surface tension of the tobacco liquid.

Figure 9:
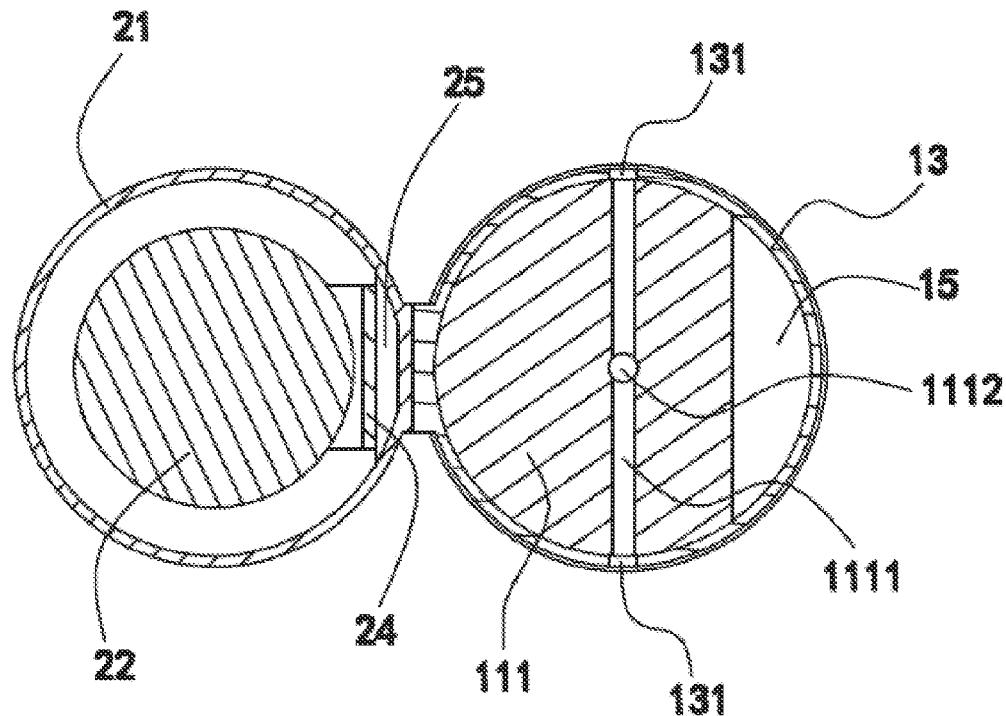
FIG. 9 is a cross-sectional view of the aerosol inhaling device of FIG. 7 taken along the line P-P'.

Referring to FIG. 9, the fixing holder 111 includes an air inlet passage 1111 and an air hole 1112 communicating with the air inlet passage 1111. The atomizing device 10 includes a housing 13 defining an air inlet 131. The air inlet 131 communicates with the air inlet passage 1111.

The atomizing device 10 further includes an atomizing head assembly 14. The atomizing head assembly 14 includes a holder 141, a heating wire assembly 142, and a cover 143. The heating wire assembly 142 is mounted on the holder 141. The cover 143 is arranged on top of the holder 141. The holder 141 includes a cavity. A sidewall of the cavity defines a through hole, and the heating wire assembly 142 passes the through hole. The holder 141 further includes an air outlet and an air pipe 1411 extending from the air outlet. The air pipe 1411 extends through the housing 13 to the power supply 20. The cover 143 defines a hole 1431 communicating with the air hole 1112 of the fixing holder 111. The liquid storage chamber 15 is defined between the atomizing head assembly 14 and the housing 13. The tobacco liquid flows to the liquid storage chamber 15 via the liquid guiding passage 1122. Two ends of the heating wire assembly 142 extend to the liquid storage chamber 15.

The heating wire assembly 142 includes a liquid conducting element 1421 and a heating wire 1422. The liquid conducting element 1421 extends through the through hole of the holder 141. The heating wire 1422 is wound around the liquid conducting element 1421, and electrically connected to the power supply 20. In the present embodiment, the liquid conducting element 1421 is a glass fiber core. It is to be noted that the liquid conducting element 1421 may be made of other materials, such as porous ceramic.

The power supply 20 includes a shell 21, a battery 22 received in the shell 21, a controller 23, and a frame 24. The controller 23 is electrically connected with the battery 22, and is configured for controlling working of the aerosol inhaling device. An air passage 25 is formed between the frame 24 and the shell 21. The air passage 25 communicates with the air pipe 1411. The mouthpiece 40 is fixedly connected with the power supply 20. The mouthpiece 40 includes a hollow part 41 communicating with the air passage 25.

The mouthpiece 40 is fixedly connected to the shell 21. When the aerosol inhaling device works, air enters the aerosol inhaling device via the air inlet 131, passes the air inlet passage 1111, the air hole 1112, the hole 1431 to the atomizing head assembly 14. The tobacco liquid is heated by the heating wire 1422 to form aerosol. The aerosol enters the air passage 25 via the air pipe 1411, and then reaches a mouth of a user through the hollow part 41 of the mouthpiece 40.

Figure 10:
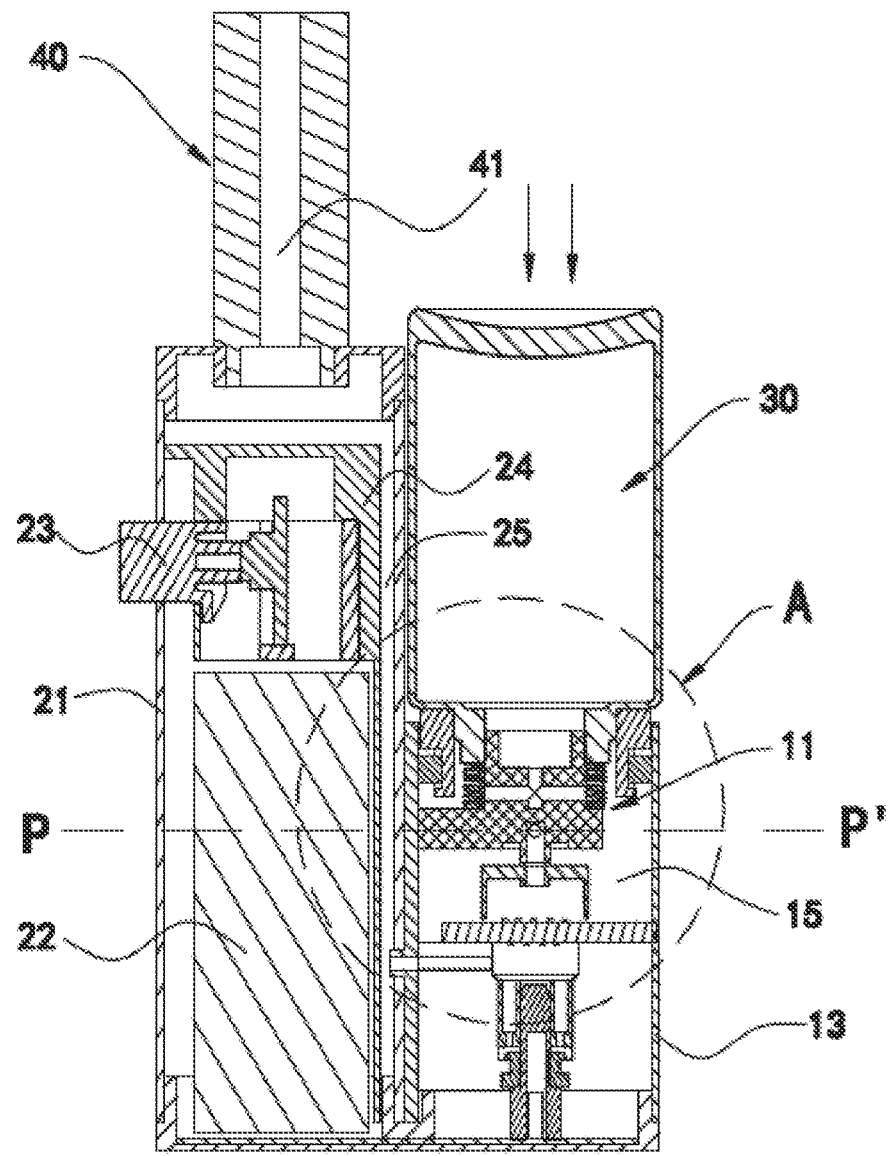
FIG. 10 is an aerosol inhaling device according to a third embodiment.

Referring to FIG. 10, the aerosol inhaling device according to the third embodiment is similar to that of the first embodiment, except that the elastic element 113 is a spring.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An aerosol inhaling device, comprising:
   a liquid supply configured for storing tobacco liquid;
   an atomizing device configured for heating the tobacco liquid to form aerosol; and
   a power supply electrically connected with the atomizing device, the power supply being configured for supplying the atomizing device power;
   wherein the liquid supply is detachably connected to the atomizing device, the atomizing device comprises a liquid controlling assembly, and the liquid controlling assembly is configured for controlling the tobacco liquid in the liquid supply to flow to the atomizing device; and
   the liquid controlling assembly comprises a liquid guiding element fixed in the atomizing device, and an elastic element engaged with the liquid guiding element; the liquid guiding element comprises a fixing holder and a liquid guiding holder extending upwards from the fixing holder; the elastic element is engaged outside the liquid guiding holder, the elastic element abuts against the liquid supply, and the liquid guiding holder inserts into the liquid supply.

2. The aerosol inhaling device according to claim 1, further comprising:
   a main body;
   the atomizing device comprising a heating element and a liquid conducting element in contact with the heating element; and
   a through hole extending from the main body to the liquid supply, the liquid conducting element extending through the through hole to the liquid supply.

3. The aerosol inhaling device according to claim 2, further comprising:
   a baffle dividing the liquid supply into a liquid storage space and a liquid conducting space;
   wherein the liquid conducting space communicates with the liquid storage space; a first end of the liquid conducting element extends to the liquid conducting space.

4. The aerosol inhaling device according to claim 3, wherein the liquid conducting space has a bottom part communicating with the liquid storage space.

5. The aerosol inhaling device according to claim 3, wherein the main body and the liquid supply are arranged side-by-side, and the liquid conducting space and the liquid storage space are provided side-by-side.

6. The aerosol inhaling device according to claim 3, wherein the main body comprises a holder separating the main body into a buffer room and a power room, the heating element is arranged in the buffer room, the through hole is defined between buffer room and the liquid conducting space, an opposite second end of the liquid conducting element extends to the buffer room, the power supply is positioned in the power room, and the buffer room defines an air inlet in a sidewall thereof.

7. The aerosol inhaling device according to claim 6, further comprising a mouthpiece communicating with the buffer room.

8. The aerosol inhaling device according to claim 6, wherein the first end of the liquid conducting element extends to a bottom part of the liquid storage space, and the second end of the liquid conducting element extends to a bottom part of the buffer room.

9. The aerosol inhaling device according to claim 1, wherein the atomizing device comprises a connector detachably connected to the liquid supply; the connector is capable of moving up and down relative to the atomizing device, so that tobacco liquid flows to the atomizing device when the liquid supply is pressed.

10. The aerosol inhaling device according to claim 1, wherein the fixing holder defines an air inlet passage and an air hole communicating with the air inlet passage; the atomizing device further comprises a housing defining an air inlet, and the air inlet communicates with the air inlet passage.

11. The aerosol inhaling device according to claim 1, wherein the atomizing device further comprises an atomizing head assembly, the atomizing head assembly has a holder, a heating wire assembly, and a cover, the heating wire assembly is mounted on the holder, the cover is arranged on top of the holder; the holder defines a cavity and a through hole passing through the cavity, the heating wire assembly extends through the through hole; the holder further comprises an air outlet and an air pipe extending from the air outlet, the air pipe extends through the housing to the power supply, the cover defines a hole communicating with the air hole of the fixing holder.

12. The aerosol inhaling device according to claim 11, wherein the liquid guiding holder defines a liquid guiding hole and a liquid guiding passage communicating with the liquid guiding hole; the atomizing head assembly and the housing cooperatively define a liquid storage chamber, the liquid guiding passage communicates with the liquid storage chamber, and two opposite ends of the heating wire assembly extend to the liquid storage chamber.

13. The aerosol inhaling device according to claim 12, wherein the elastic element defines a plurality of gaps communicating with the liquid guiding passage.

14. An aerosol inhaling device, comprising:
   a liquid supply configured for storing tobacco liquid;
   an atomizing device configured for heating the tobacco liquid to form aerosol, the atomizing device being arranged side-by-side with the liquid supply along a vertical direction; and
   a power supply electrically connected with the atomizing device, and being configured for supplying the atomizing device power, the power supply being arranged side-by-side with the atomizing device along a horizontal direction perpendicular to the vertical direction; the power supply has a shell, a battery received in the shell, a controller and a frame disposed beside the battery; at least a pipe spatially communicable between the frame of the power supply and the atomizing device for aerosol formed by the atomizing device flowing toward outside of the frame of the power supply for inhaling.

* * * * *